United States Patent [19]

Carroll et al.

[11] Patent Number: 4,568,757
[45] Date of Patent: Feb. 4, 1986

[54] CONFIGURATIONALLY LOCKED RETINOIDS

[75] Inventors: Frank I. Carroll, Durham; Anita H. Lewin, Chapel Hill, both of N.C.

[73] Assignee: Research Triangle Institute, Research Triangle Park, N.C.

[21] Appl. No.: 574,741

[22] Filed: Jan. 30, 1984

[51] Int. Cl.$^4$ ................. C07D 309/30; C07D 211/88; C07C 69/618; C07C 57/34
[52] U.S. Cl. .................................. 549/294; 514/859; 514/863; 546/290; 546/301; 546/350; 549/273; 560/80; 560/81; 560/127; 560/190; 562/488; 562/489; 562/501; 562/509; 562/595
[58] Field of Search ............... 560/127, 81, 80, 190; 562/509, 489, 488, 501, 595; 549/294, 273; 546/350, 290, 301

[56] References Cited
U.S. PATENT DOCUMENTS
4,105,855  8/1978  Schulz et al. ..................... 560/190

OTHER PUBLICATIONS
Lewin et al., The Journal of Organic Chemistry, 48, 222–227, Jan. 28, 1983.

Primary Examiner—Natalie Trousof
Assistant Examiner—Vera C. Clarke
Attorney, Agent, or Firm—Cushman, Darby & Cushman

[57] ABSTRACT

A group of retinoids having "vitamin A type" activity which have the structure

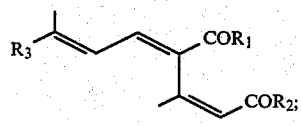

I.

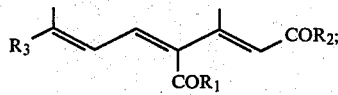

II.

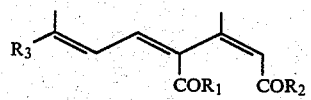

III.

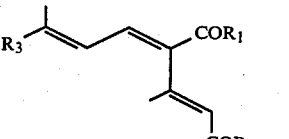

IV.

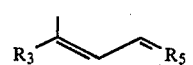

V.

wherein R3 is a trimethylcyclohexenylethylene, tetramethyltetrahydronaphthalene or methoxytrimethylphenylethylene group;

R1 and R2 which are different are selected from —OH, —OR4 and —NHR, provided one of R1 and R2 is OH; R4 is alkyl of 1 to 20 carbons; and R is selected from the group consisting of hydrogen, alkyl of 1 to 4 carbons, hydroxyalkyl of 1 to 4 carbons, alkylhydroxyalkyl of 1 to 4 carbons, phenyl, hydroxyphenyl and carboxyphenyl, and R5 is a lactone or lactam of the structure

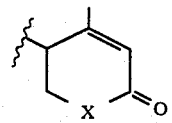

(i)

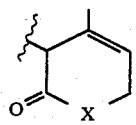

(ii)

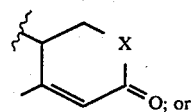

(iii)

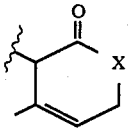

(iv)

and X is oxygen or NR where R is as above, and the pharmaceutically acceptable salts thereof.

11 Claims, No Drawings

CONFIGURATIONALLY LOCKED RETINOIDS

FIELD OF THE INVENTION

This invention relates generally to the field of retinoids and, in particular, to a new class of 12-substituted retinoids which exhibit "vitamin A type" activity.

BACKGROUND OF THE INVENTION

"Vitamin A type activity" is found in species which possess properties effecting cell growth and differentiation. Naturally occurring compounds possessing such activity are retinol, retinal and retinoic acid. All are unacceptable for use in humans since they are toxic and some of them accumulate in the liver. Thus, much effort has been devoted to developing retinoids having high activity (which may therefore be administered in low doses and yet be effective) and relatively low, if any, side effects. "Vitamin A activity" can be determined by numerous tests; it has been shown that a good correlation exists between the Tracheal Organ Culture (TOC) screen, in which reversal of keratinization is determined, and "vitamin A activity".

The use of retinoic acid in the treatment of acne vulgaris is known. Clinical trials in Europe have also been reported in which the effect of retinoic acid on epithelial tumors was discussed.

Two retinoids are in current use as prescription drugs for the treatment of acne and psoriasis, namely Isoretinoin and Etretinate, and have the following structure:

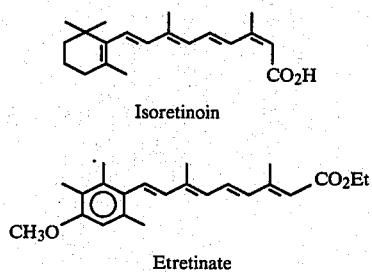

Isoretinoin

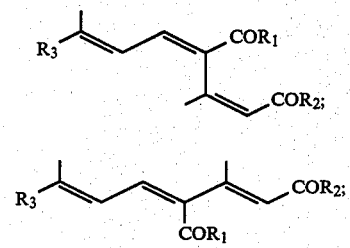

Etretinate

It is the primary object of the present invention to provide a new group of retinoids which display "vitamin A type activity". This and other objects of the present invention will become more apparent from the discussion which follows.

SUMMARY OF THE INVENTION

In general, the present invention provides a new and useful group of retinoids which display vitamin A type activity and which possess the chemical structure

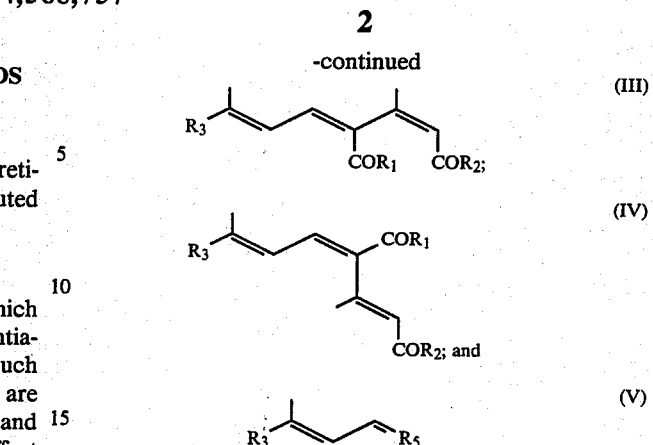

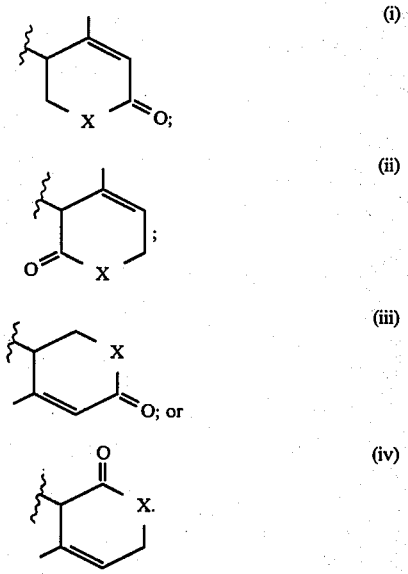

wherein $R_3$ is a trimethylcyclohexenylethylene, tetramethyltetrahydronaphthalene or methoxytrimethylphenylethylene group;
wherein
$R_1$ and $R_2$, which are different are selected from —OH, —OR$_4$ and —NHR, provided one of $R_1$ and $R_2$ is OH; $R_4$ is alkyl of 1 to 20 carbons; and R is selected from the group consisting of hydrogen, alkyl of 1 to 4 carbons, hydroxyalkyl of 1 to 4 carbons, alkylhydroxyalkyl of 1 to 4 carbons, phenyl, hydroxyphenyl and carboxyphenyl, and $R_5$ is a lactone or lactam of the structure and X is oxygen or NR where R is as defined above, and the pharmaceutically acceptable salts thereof.

The retinoids of structures I, II, III and IV may be considered as half-esters or half-acids, while those of structure V are lactams or lactones.

While one of $R_1$ and $R_2$ may be —OR$_4$ or —NHR, the ester grouping —OR$_4$ are preferred, especially those of alkyl groups of 1 to 5 carbons, methyl, ethyl, N-propyl, isopropyl, N-butyl.

In those instances where one of $R_1$ and $R_2$ is —NHR, R may be selected from the class noted above, suitably including methyl; ethyl, n-propyl; n-butyl; hydroxyethyl; hydroxypropyl; 2,3-dihydroxypropyl; 1-methyl-3-hydroxypropyl; 4-hydroxybutyl; phenyl; 2-hydroxyphenyl; 3-hydroxyphenyl; 4-hydroxyphenyl; and 2, 3 or 4-carboxyphenyl.

$R_3$ is of the structural formula:
(a) trimethylcyclohexenylethylene

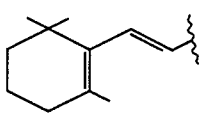

(b) tetramethyltetrahydronaphthalene

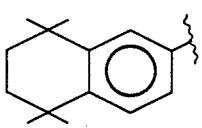

(c) methoxytrimethylphenylethylene

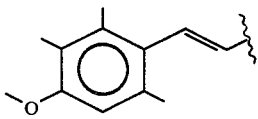

and preferably is trimethylcyclohexenylethylene.

These compounds and their pharmaceutically acceptable salts may be combined with pharmaceutically acceptable carriers in the form of a lotion, cream or gel for topical application or alternatively, if desired, compounded into tablet form or as an elixar for internal application.

DETAILED DESCRIPTION OF THE INVENTION

For convenience and to facilitate better understanding of the discussion below, the following numbered structural formulas are given:

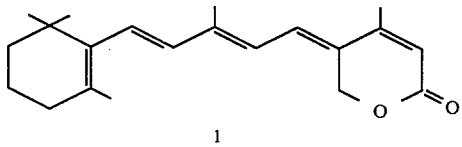

1

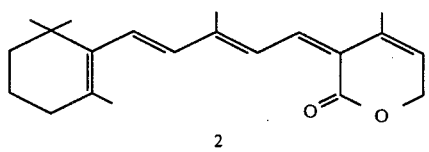

2

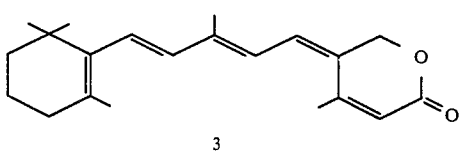

3

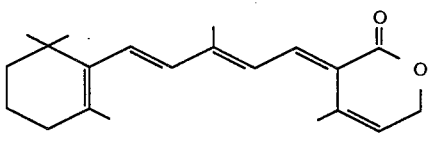

4

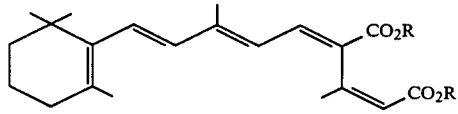

5, R = H
5E, R = $CH_3$

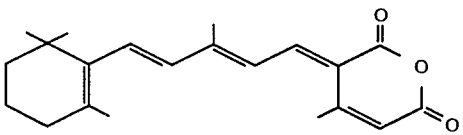

6

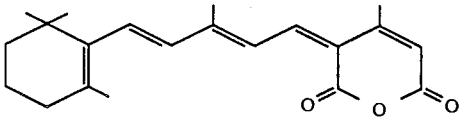

7

Treatment of the anhydride 7 with methanolic potassium hydride produced a mixture of two new retinoids in an approximately 10:1 ratio. These were expected to be monomethyl esters of 13-cis-12-carboxyretinoic acid (8,9). Purification of the major

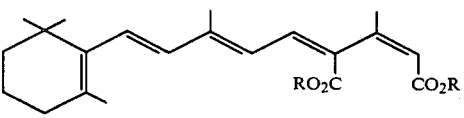

8, R = H; R' = $CH_3$
9, R = $CH_3$; R' = H component by column chromatography did indeed give a retinoid monomethyl ester, but its $^1H$ and $^{13}C$ NMR spectra resembled those of 11-cis,13-cis-12-carboxyretinoic acid (5) and its dimethyl ester 5E. Thus, although the 25.6-ppm resonance for the 13a-methyl in the $^{13}C$ NMR spectrum of this monomethyl ester is consistent with both 13-cis- and 11-cis,13-cis-12-carboxyretinoic acid and the analogous dimethyl esters (10 and 5, respectively), the chemical shifts of H-10 and H-11 in the $^1H$ NMR spectrum are inconsistent with a 13-cis structure (e.g., by comparison with 10). Reduction of this monomethyl ester with lithium aluminum hydride, followed by water removal, gave a lactone whose $^1H$ NMR spectrum exhibited singlet signals at 4.78 and 5.79 ppm for the 12a-methylene and H-14, respectively, pointing to reduction having taken place at the 12a-position. In other words, this is the δ-lactone of 12-(hydroxymethyl)retinoic acid. Since the carbomethoxy group would be reduced in preference to the carboxy group in a half-ester/half-acid, it follows that the structure of the monomethyl ester is 11-cis,13-

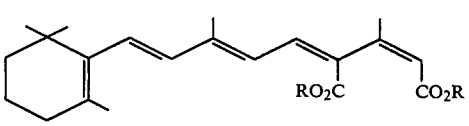

10, R = H
10E, R = $CH_3$

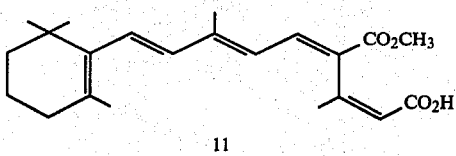

11 cis-12-carbomethoxyretinoic acid (11), and that of the lactone is 11-cis,13-cis-12-(hydroxymethyl)retinoic acid δ-lactone (3). It thus appeared that the saponification of the anhydride 7 was taking place with concomitant isomerization of the 11,12 double bond. Whereas facile photoisomerization of the anhydride 7 to its 11-cis isomer 6 has been observed, these reactions, like all the work described herein, were carried out under dim red lights, precluding photoisomerization. When the product mixture from the saponification of 7 was immediately reduced without purification and the product subjected to water removal, two lactones were formed which were both different from 3. Spectral examination after chromatographic separation showed both products to lack the C-13a signals at ca. 25 ppm which are so characteristic of the 11-cis,13-cis geometry, displaying instead signals at 18.0 and 19.7 ppm, respectively, suggestive of a cyclic 13-cis structure such as 7 (Table I). The $^1$H NMR spectra (Table II) serve to pinpoint the position of the carbonyl group. Thus, the chemical shifts of H-10 and H-11 are upfield in the major product relative to their positions in the minor product and in model compounds such as 7 and are similar to those in 3. Taken together with the singlet nature of the H-14 signal at 5.68, the absence of a carbonyl group at C-12a for the major product is suggested, and its structure is therefore 13-cis-12-(hydroxymethyl)retinoic acid δ-lactone (1). That the structure of the minor product is 13-cis-12-carboxyretinol δ-lactone (2) is confirmed by the H-14 triplet at 5.66 ppm, due to coupling with the methylene hydrogens at C-15.

On the basis of these structures, it appears that the methanolic saponification of 13-cis-12-carboxyretinoic anhydride (7) proceeds to give mainly 13-cis-12-carbomethoxyretinoic acid (8) with methyl 13-cis-12-carboxyretinoate (9) as a byproduct. However, this product mixture is not stable and, upon attempted purification, leads to the 11-cis,13-cis half-ester 11. In fact, when the course of the reaction was followed by high-pressure liquid chromatography (HPLC), it was found that immediately after addition of the base, the product mixture consisted of only two components in approximately a 10:1 ratio. After 30 min., a third component, coincident with 11-cis,13-cis-12-carbomethoxyretinoic acid (11), appeared at the expense of the major component, of the initial product mixture. At the end of 2 h 11 was the predominant product. Since potassium ion is known to lead to isomerization in retinoid systems as taught in French Pat. No. 1,320,153, the reaction was carried out by using sodium hydroxide; identical results were obtained. The initial product mixture could be isolated by quenching and workup immediately after disappearance of the starting anhydride 7 (<5 min.). It could be kept as an oil almost without change at −70° C. for about 1 week. At room temperature the half-ester 11 appeared within 1 day; in methanol solution the product composition changed within a few hours, and this was accelerated by the addition of base. It therefore appears that the 13-cis half-esters 8 and 9 are the primary saponification products of the anhydride 7. The major product 8 isomerizes rapidly to the 11-cis,13-cis half-ester 11 (Scheme I).

Similar results had been obtained when methylation of 13-cis-12-carboxyretinoic acid (10) was attempted. Thus, treatment of 10 with methanolic hydrochloric acid led to isomerization (see Lewin et al, *J. Org. Chem.*, 1982, 47, 1799–1807), but analogous treatment of 11-cis,13-cis-12-carboxyretinoic acid (5) gave a new monomethyl ester, whose $^1$H NMR was very similar to those of 11, 5 and 5E. It therefore followed that the structure of this monomethyl ester was methyl 11-cis,13-cis-12-carboxyretinoate (12). This was confirmed by Scheme I$^a$

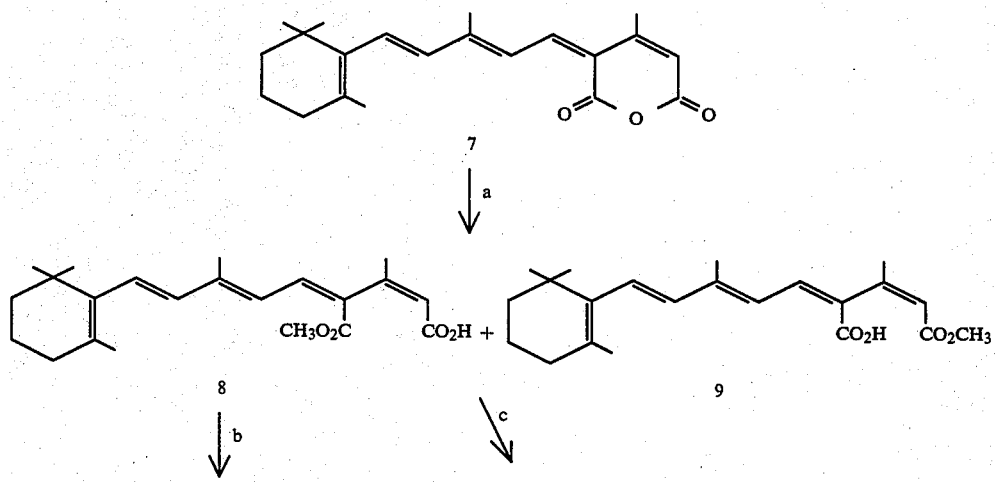

-continued
Scheme I[a]

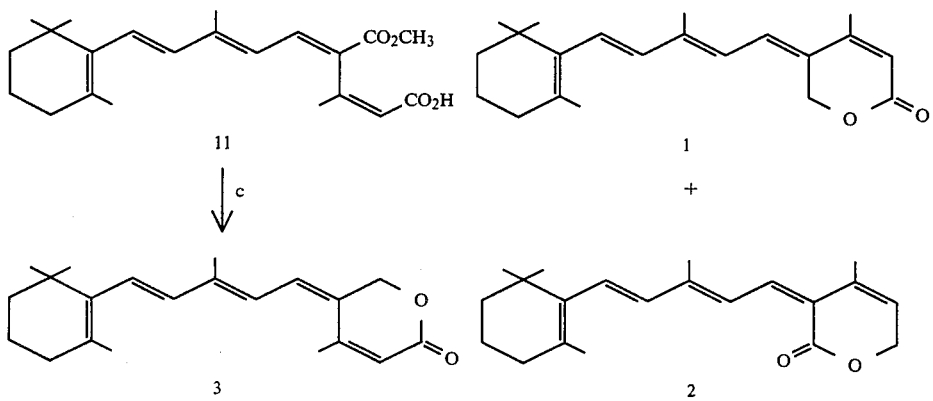

[a] (a) KOH/MeOH; (b) column chromatography; (c) LiAlH$_4$—H$_2$O.

reduction with lithium aluminum hydride, which gave a hydroxy acid 13, the $^1$H NMR of which exhibited a triplet at 5.66 ppm for H-14; the balance of the vinyl region of the spectrum was essentially superimposable with the spectra of 5, 5E, and 12. Dehydration of 13 gave a lactone, the NMR parameters of which were perfectly consistent with the assigned structure, 11-cis,13-cis-12-carboxyretinol δ-lactone (4, Scheme II).

Having in hand the 11-cis,13-cis half-esters (11 and 12) and lactones (3 and 4), we could easily verify the lack of isomerization of the other 13-cis half-ester 9 (minor product) in spite of the small amount present. Specifically, the 11-cis,13-cis half-ester 12 was not detected even after leaving the product mixture 8 and 9 in basic methanol solution for long time periods, nor was the lactone 4 ever detected among the reduction-dehydration products. Control experiments showed that both 12 and 4 would have survived the reaction conditions had they been formed. It, therefore, follows that Scheme II[a]

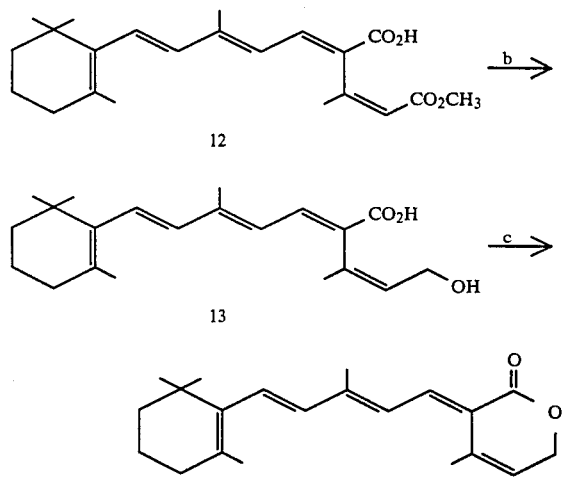

[a] (a) 3% HCl/MeOH; (b) LiAlH$_4$/THF, (c) —H$_2$O.

although the major primary product, 13-cis-12-carbomethoxyretinoic acid (8), isomerizes readily to the 11cis,13-cis analogue 11, the minor primary product, methyl 13-cis-12-carboxyretinoate (9) does not isomerize to its 11-cis,13-cis analogue 12.

TABLE I $^{13}$C NMR Spectral Data (ppm) of Retinoids[a]

| compd | \_\_ carbon no. \_\_ | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 1a | 5a | 9a | 13a | 12a |
| 1 | 34.8 | 40.2 | 19.7 | 33.5 | 130.8 | 138.2 | 129.9 | 138.0 | 138.0 | 125.2 | 124.6 | 142.1 | 151.6 | 117.1 | 151.6 | 29.1 | 21.8 | 12.3 | 18.0 | 67.4[b] |
| 2[c] | 34.8 | 40.2 | 19.7 | 33.7 | 131.5 | 138.4 | 131.4 | 138.4 | 138.1 | 129.9 | 134.2 | 143.1 | 134.1 | 119.9 | 76.1 | 29.5 | 22.3 | 12.9 | 19.7 | |
| 3 | 34.8 | 40.0 | 19.7 | 33.5 | 130.5 | 138.3 | 130.0 | 138.3 | 142.2 | 126.0 | 129.0 | 128.5 | 152.0 | 119.6 | 163.8 | 29.1 | 21.8 | 12.0 | 24.5 | 64.7 |
| 4 | 34.7 | 40.1 | 19.7 | 33.5 | 130.7 | 138.4 | 130.8 | 138.4 | 145.6 | 126.4 | 132.7 | 123.1 | 133.5 | 123.7 | 66.8 | 29.1 | 21.8 | 12.2 | 22.2 | 166.4 |
| 11 | 35.0 | 40.4 | 19.9 | 33.7 | 131.0 | 138.3 | 131.7 | 137.7 | 145.4 | 125.4 | 134.1 | 131.6 | 152.4 | 120.8 | 166.4 | 29.2 | 22.0 | 13.1 | 25.6 | |
| 12 | 34.8 | 40.1 | 19.7 | 33.5 | 130.5 | 138.3 | 130.5 | 138.1 | 144.1 | 125.5 | 133.2 | 132.8 | 152.4 | 120.5 | 165.4 | 29.2 | 21.9 | 12.7 | 25.4 | 166.0 |
| 13 | 34.7 | 40.1 | 19.7 | 33.5 | 131.5 | 138.1 | 130.9 | 138.2 | 144.3 | 126.4 | 135.7 | 130.5 | 132.4 | 130.6 | 60.2 | 29.1 | 21.7 | 12.7 | 23.6 | 167.6 |

[a] At 25.034 MHz in dioxane-d$_8$ unless otherwise noted.
[b] In CD$_3$CN.
[c] Recorded in CDCl$_3$; chemical shifts corrected to dioxane-d$_8$ by addition of +0.6 ppm.

TABLE II

Proton NMR Spectral Data (ppm) of Retinoids[a]

| | | | | | proton on carbon no. | | | | | | |
|---|---|---|---|---|---|---|---|---|---|---|---|
| compd | 7 | 8 | 10 | 11 | 14 | 1a | 5a | 9a | 13a | 15 | 12a |
| 1 | 6.37 | 6.21 | 6.27 | 6.81 | 5.68 | 1.04 | 1.71 | 2.03 | 2.11 | | 5.78 |
| 2 | 6.38 | 6.38 | 7.65 | 7.00 | 5.75 | 1.00 | 1.69 | 1.97 | 2.02 | 4.83 | |
| 3 | 6.38 | 6.21 | 6.63 | 6.73 | 5.79 | 1.03 | 1.72 | 2.00 | 2.30 | | 4.78 |
| 4 | 6.41 | 6.19 | 6.71 | 7.77 | 5.89 | 1.04 | 1.72 | 2.10 | 2.10 | 4.88 | |
| 11 | 6.35 | 5.99 | 5.96 | 7.44 | 5.88 | 0.98 | 1.66 | 1.98 | 2.00 | | |
| 12 | 6.38 | 6.12 | 5.98 | 7.45 | 5.90 | 1.02 | 1.67 | 2.00 | 2.00 | | |
| 13 | 6.34 | 6.18 | 6.06 | 7.60 | 5.65 | 1.03 | 1.69 | 1.85 | 2.04 | 3.78 | |

[a] At 100 MHz in dioxane-$d_8$.

TABLE III

HPLC Retention Times for Retinoids

| no. | retinoid name | column[a] | eluant[a] | retention time, min. |
|---|---|---|---|---|
| 1 | 13-cis-12-(hydroxymethyl)retinoic acid-lactone | B | C | 11.0 |
| 2 | 13-cis-12-carboxyretinol-lactone | B | C | 6.7 |
| 3 | 11-cis,13-cis-12-(hydroxymethyl)retinoic acid-lactone | B | C | 13.5 |
| 4 | 11-cis,13-cis-12-carboxyretinoic acid-lactone | A | D | 4.0 |
| 8 | 13-cis-12-carbomethoxyretinoic acid | A | D | 8.0 |
| 9 | methyl 13-cis-12-carboxyretinoate | A | D | 6.5 |
| 11 | 11-cis,13-cis-12-carbomethoxyretinoic acid | A | D | 9.0 |
| 12 | methyl 11-cis,13-cis-12-carboxyretinoate | A | D | 4.0 |

[a] A, Radial Pak A; B, Radial Pak B; C, 10% $Et_2O$/90% hexane; D, 0.2% $NH_4OAc$/60% $CH_3CN$/40% $H_2O$ In summary, it is noteworthy that although 11-cis,13-cis-12-carboxyretinoic anhydride (6) isomerized rapidly in the dark to 13-cis-12-carboxyretinoic anhydride (7) and 13-cis-12-carbomethoxyretinoic acid (8) isomerized readily to 11-cis,13-cis-12-carbomethoxyretinoic acid (11), the target δ-lactones 1-4 were stable to isomerization.

The following equipment and procedures were utilized in carrying out the experimental work described herein.

Melting points were determined on a Thomas-Hoover capillary tube apparatus or on a Koffler hot stage, and they are uncorrected. Infrared spectra were recorded on a Perkin-Elmer Model 267 grating spectrophotometer, ultraviolet spectra were recorded on a Cary 14 spectrophotometer, and mass spectra were obtained on an AEI MS-901 spectrometer. Proton NMR spectra were recorded on a Varian HA-100 spectrometer and $^{13}C$ NMR spectra were determined on a JEOL JNM-PS-10 NMR instrument. $^{1}H$ NMR and $^{13}C$ NMR data are summarized in Tables I and II.

Analytical chromatography was carried out by using commercial silica gel F-254 for TLC and a Waters Associates high-pressure liquid chromatograph consisting of two constant-flow pumps (M6000A) controlled electronically by a solvent programmer (Model 660), a septumless nonstop-flow high-pressure injector (Model U6-K), and a variable-wavelength UV detector (Model 450). The columns used were Waters Associates 3.9 mm×30 cm μ-Porasil, μ-Bondapak $C_{18}$, and Radial Pak A and B cartridges.

Preparative separations were accomplished by using silica gel prepacked columns for medium-pressure liquid chromatography and two 10 mm×25 cm Partisil 10 columns in series or a 4 mm×25 cm column for high-pressure chromatography.

All laboratory operations involving retinoids and related polyene systems were performed under dim red lights and in an inert atmosphere.

The following examples are offered to more fully illustrate the invention but are not to be construed as limiting the scope thereof.

EXAMPLE ONE

Methyl 11-cis,13-cis-12-Carboxyretinoate (12)

A solution of 1.50 g (0.004 mol) of 11-cis,13-cis-12-carboxyretinoic acid (5) in 3% methanolic HCl was stirred at room temperature for 6 h. The solvent was removed in vacuo, and the residue was dissolved in $Et_2O$, washed with $H_2O$ and brine, and dried ($Na_2SO_4$). The crude ester (1.49 g) was purified by elution on a medium-pressure silica gel column (size B) by using 1% MeOH in 2:1 hexane-EtOAc to yield 650 mg (36%) of a solid: mp 130°-133° C.; IR (KBr) 1675, 1720 $cm^{-1}$, UV (MeOH) $\lambda_{max}$ 327 nm (ε33240); mass spectrum, calcd for $C_{22}H_{30}O_R$ m/e 358.215, found m/e 358.215.

EXAMPLE TWO 11-cis,13-cis-12-Carbomethoxyretinoic Acid (11)

To a slurry of 200 mg (0.6 mmol) 13-cis-12-carboxyretinoic anhydride (7) in 10 mL of MeOH was added 3.1 mL (3 mmol) of 1N KOH in MeOH. Immediate dissolution of the solid and a color change took place. TLC (silica gel; acetone-hexane, 1:1) showed the anhydride to be completely consumed. The reaction mixture was quenched with saturated aqueous $NH_4Cl$ and extracted with $Et_2O$. After drying and evaporation, the organic phase yielded 142 mg of a yellow powder, mp 129°-135° C. Chromatography of 70 mg of the powder on a size-A prepacked silica gel column, by eluting with 25% acetone-hexane at 2 mL/min and collecting 0.5-mL fractions, gave 23 mg of relatively pure material with $^{1}H$ NMR and $^{13}C$ NMR spectra consistent with a monomethyl ester of 11-cis,13-cis-12-carboxyretinoic acid. Mass spectral analysis gave the following: calcd for $C_{22}H_{30}O_4$ m/e 358.2143, found/me 358.2139.

EXAMPLE THREE

11-cis,13-cis-12-(Hydroxymethyl)retinoic Acid δ-Lactone (3)

To a stirred suspension of 4.0 g (12.2 mmol) of 13-cis-12-carboxyretinoic anhydride (7) in 120 mL of MeOH at 0° C. was slowly added 48 mL of 1N KOH in MeOH, and the reaction mixture was stirred for 2 h. It was then quenched with $H_2O$ and extracted with $Et_2O$. The aqueous phase was cooled to 0° C., quenched with saturated aqueous $NH_4Cl$, and extracted with $Et_2O$. These ethereal layers were back-washed with brine, dried over $Na_2SO_4$, and evaporated to give 4.02 g of an oil which was shown by HPLC to consist primarily of 11. It was dissolved in 10 mL of THF (freshly distilled from $LiAlH_4$) and added slowly to a cold ($-15°$ C.) slurry of 1.06 g (30 mmol) of $LiAlH_4$ in 140 mL of THF. After stirring at $-15°$ C. for 15 min., the reaction was quenched with saturated aqueous $NH_4Cl$, diluted with $H_2O$, acidified to pH 5 with 10% $H_2SO_4$, and extracted with EtOAc. The residue, after evaporation of the EtOAc, was subjected to dehydration by azeotroping it five times with cyclohexane at room temperature, TLC indicated two nonpolar components and one polar component. Separation on a cleanup column (silica gel, 2:1 EtOAc/hexane) gave a small amount (488 mg) of a mixture of the nonpolar components 1 and 2. The majority of the material was the polar component (2.1 g); this hydroxy acid was refluxed with cyclohexane with water removal by a Dean-Stark trip for 1 h. HPLC and TLC analses indicated mainly one component which was purified by crystallization from EtOAc. The pure compound was shown to be the lactone 3: mp 165°–169° C.; IR (KBr) 1700 cm$^{-1}$; UV (EtOH) $\lambda_{max}$ 365 nm ($\epsilon$ 33225); mass spectrum, calcd for $C_{21}H_{28}O$ m/e 312.2089, found m/e 312.2086.

EXAMPLE FOUR

13-cis-12-(Hydroxymethyl)retinoic Acid δ-Lactone (1) and 13-cis-12-Carboxyretinol δ-Lactone (2)

To a stirred suspension of 4.0 g (12.2 mmol) of 13-cis-12-carboxyretinoic anhydride (7) in 120 mL of MeOH at 0° C. was slowly added 48 mL of 1N KOH in MeOH. The solution, which had turned almost colorless, was stirred at room temperature for 30 min. At the end of this time, it was quenched with saturated aqueous $NH_4Cl$ at 0° C., extracted with $Et_2O$, and back-washed with brine. The organic phase was dried over anhydrous $Na_2SO_4$ and evaporated to give ca. 5 g of an oil which was dissolved in 30 mL of THF (freshly distilled from $LiAlH_4$) and very slowly added to a stirred slurry of 1.31 g (32.5 mmol) of $LiAlH_4$ in 140 mL of THF at $-15°$ C. Stirring was continued at $-15°$ C. for 15 min, at the end of which the reaction was quenched with saturated aqueous $NH_4Cl$, diluted with $H_2O$, and acidified to pH 5 with 10% $H_2SO_4$. The mixture was then extracted with EtOAc, and the combined organic extracts were evaporated. The residue was subjected to dehydration by dissolution in cyclohexane and evaporation at room temperature (five times). Since TLC still showed the presence of polar material (hydroxy acids), the cyclohexane dehydration was repeated at 60° C. HPLC analysis of the residue showed two components to be present; these were separated by medium-pressure liquid chromatography using silica gel prepacked columns and eluting with 20–50% $Et_2O$/hexane. The fastest eluting component was 13-cis-12-carboxyretinol δ-lactone (2): IR (KBr) 1710 cm$^{-1}$; UV (EtOH) $\lambda_{max}$ 367 nm ($\epsilon$ 18257); mass spectrum, calcd for $C_{21}H_{28}O_2$ m/e 312.2089, found m/e 312.2086. The slower eluting fraction was predominantly 13-cis-12-(hydroxymethyl)-retinoic acid δ-lactone (1) contaminated with traces of 2. Crystallization from $Et_2O$-hexane gave a pale yellow solid: mp 101°–103° C.; IR (KBr) 1700 cm$^{-1}$; UV (EtOH) $\lambda_{max}$ 368 nm ($\epsilon$ 28500); mass spectrum calcd for $C_{21}H_{28}O_2$ m/e 312.2089, found m/e 312.2086.

EXAMPLE FIVE

11-cis,13-cis-12-Carboxyretinol δ-Lactone (4)

To a cold ($-15°$ C.) slurry of 118 mg (3.12 mmol) of $LiAlH_4$ in 50 mL of THF was slowly added a solution of 560 mg (1.56 mmol) of methyl 11-cis,13-cis-12-carboxyretinoate (12) in 10 mL of THF. After being stirred for 5 min, the reaction mixture was quenched with a saturated solution of $NH_4Cl$, diluted with $H_2O$, and extracted with $Et_2O$. The organic phase was washed with $H_2O$ and brine and dried ($Na_2SO_4$). The crude hydroxy acid 13 (490 mg) was refluxed in 25 mL of cyclohexane by using a Dean-Stark water separator for 6 h, and the solvent was then removed in vacuo. The product was purified by elution on a medium-pressure silica gel column (size B) by using 40% $Et_2O$ in hexanes to yield 185 mg (38%) of a gum whose spectra showed it to be 11-cis,13-cis-12-carboxyretinol δ lactone (4): IR (KBr) 1710 cm$^{-1}$; UV (MeOH) $\lambda_{max}$ 365 nm ($\epsilon$ 20530); mass spectrum, calcd for $C_{21}H_{28}O_2$ m/e 312.209, found m/e 312.209.

EXAMPLE SIX

Reaction of 13-cis-12-Carboxyretinoic Anhydride (7) with Methanolic Potassium Hydroxide To a 1-mL Reacti-Vial containing 1 mg (0.003 mmol) of 13-cis-12-carboxyretinoic anhydride (7) were added 100 μL of MeOH and 3 μL (0.003 mmol) of KOH/MeOH. The reaction was monitored by HPLC. After 0.5 h, the major product was 13-cis-12-carbomethoxyretinoic acid (8), accompanied by trace amounts of methyl 13-cis-12-carboxyretinoate (9). Heating of the isolated product mixture for 2 h gave mainly 11-cis,13-cis-12-carbomethoxyretinoic acid (11) with minor amounts of 8 and 9. The identical mixture was obtained by heating the reaction mixture (without isolation) for 2 h. Identical results were obtained by using NaOH. None of the isomeric methyl 11-cis,13-cis-12-carboxyretinoic acid (12) was detected in any stage, although it would have been detectable by HPLC had it been present.

HPLC Analysis

The best separations were achieved by using Radial Pak cartridges, although stainless steel columns gave similar results. The half-esters were analyzed by using Radial Pak A with 60% $CH_3CN$/40% $H_2O$/0.25% $NH_4OAc$ (2 mL/min) as the eluant; detection was at 350 nm. The lactones were analyzed on Radical Pak B with 2 mL/min of 1:9 $Et_2O$/hexane; detection was at 350 nm. The retention data are shown in Table III. The solvents were degassed prior to use.

Test results on the compound of Example One (12), it corresponding diacid (5) and corresponding dimethylester (5E) in the TOC screen revealed surprising results. At a concentration of $10^{-9}M$, the diacid (5) was found to have activity in 3 of 6 cultures and the related dimethyl ester (5E) was found to be inactive. This means that under the test conditions (5E) is not undergoing conversion to (5), either enzymatically or hydrolytically because, if it were, activity should have been observed. Partial hydrolysis could lead to the half-esters which, based on the observed lack of activity of (5E) might be expected to have no activity either. Unexpectedly, the half-ester (12) has activity in 4 of 4 cultures at $10^{-9}$M.

While the foregoing discussion is directed primarily to trimethylcyclohexenylethylene derivatives, it will be appreciated that with but small revisions one may also prepare the desired tetramethyltetrahydronaphthalene and methoxytrimethylphenylethylene in which instance $R_3$ may be either

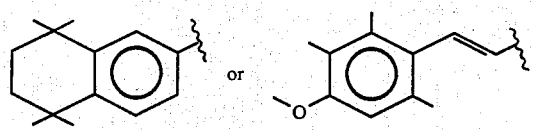

In addition, preparation of the various half-amide derivatives may be readily facilitated according to the synthesis outlined in Scheme III below.

SCHEME III
Preparation of 12-Carboxyretinoid Amides (exemplified for the 11-cis,13-cis isomer)

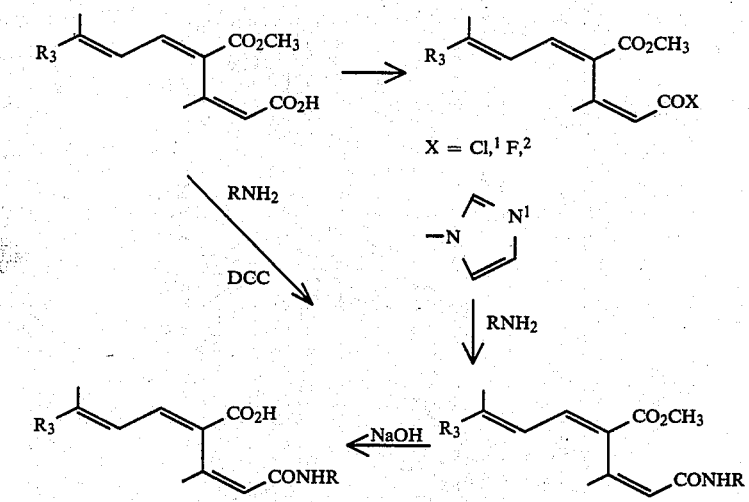

1. M. B. Sporn and D. L. Newton in "Inhibition of Tumor Induction and Development", M. S. Zedeck and M. Lipkin, Eds., Plenum Press, New York (1981).
2. A. B. Barus and J. A. Olson, Fed. Proc., 40, 1803 (1981); ibid, 41, 387 (1982); Biochim. Biophys. Acta., 757, 288 (1983).

For $R_3 =$

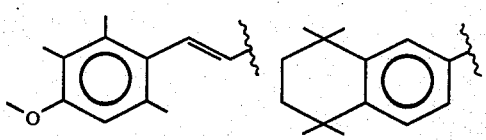

Schemes IV and V show the preparations of the starting material.

SCHEME IV
(Tetramethyltetrahydronaphthalene Derivatives)

Synthesis of

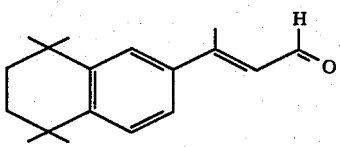

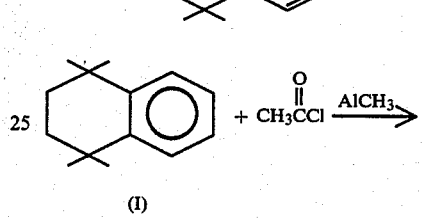

(I)

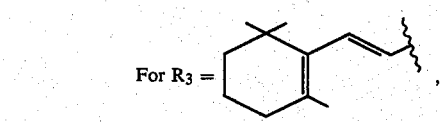

the starting material, trans-β-ionylideneacetaldehyde, is commercially available.

-continued

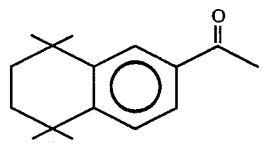

β-ionene analog

↓ (Wittig of silane)

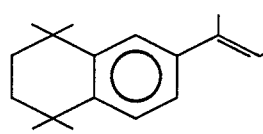

β-ionylideneacetaldehyde analog (I) E. Giovanni and K. Brandenberger, Hlv. Chim. Acta, 56, 1775 (1973).

SCHEME V (Methoxytrimethylphenylethylene Derivatives)

Synthesis of

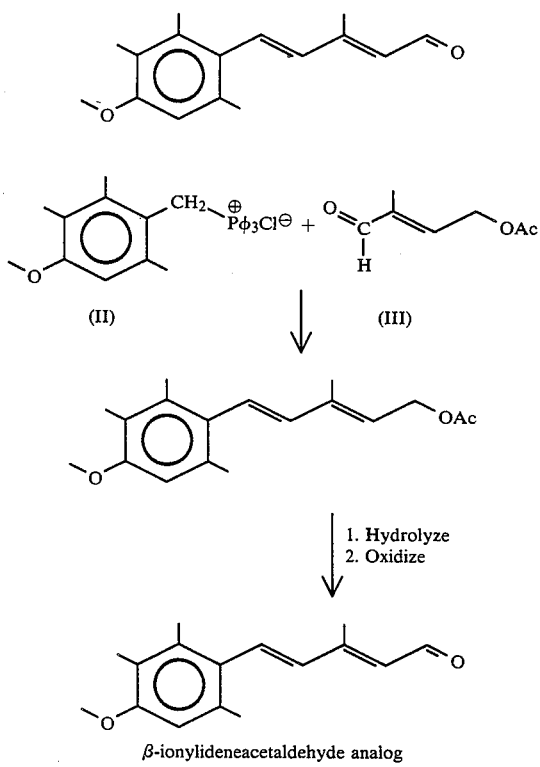

β-ionylideneacetaldehyde analog (II) W. Bollag, R. Ruegg, G. Ryser, U.S. Pat. No. 4,163,103, July 31, 1979.

(III) J. F. W. Keana, P. E. Eckler, J. Org. Chem., 41, 2625 (1976).

We claim:

1. A retinoid having the structure selected from

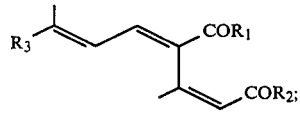 (I)

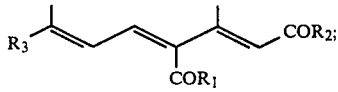 (II)

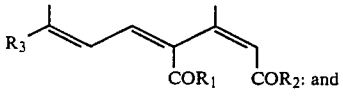 (III)

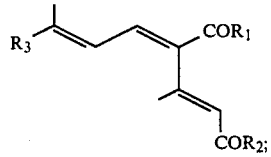 (IV)

wherein $R_3$ is selected from the structural formula consisting of

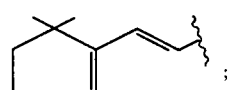 (a)

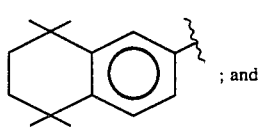 (b)

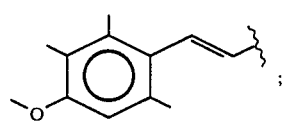 (c)

wherein
$R_1$ and $R_2$, which are different are selected from —OH, —OR$_4$ and —NHR, provided one of $R_1$ and $R_2$ is OH; $R_4$ is alkyl of 1 to 20 carbons; and R is selected from the group consisting of hydrogen, alkyl of 1 to 4 carbons, hydroxyalkyl of 1 to 4 carbons, alkylhydroxyalkyl of 1 to 4 carbons, phenyl, hydroxyphenyl and carboxyphenyl, and the pharmaceutically acceptable salts thereof.

2. The retinoid of claim 1 having the Structure I wherein $R_3$ is formula (a) and $R_1$ or $R_2$ is alkyl of 1 to 20 carbons.

3. The retinoid of claim 2 wherein $R_1$ or $R_2$ is alkyl of 1 to 5 carbons.

4. Methyl 11-cis,13-cis-12-carboxyretinoate and the pharmaceutically acceptable salts thereof.

5. 11-cis,13-cis-12-carbomethoxyretinoic acid and the pharmaceutically acceptable salts thereof.

6. A retinoid having the structure

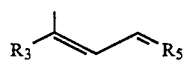

wherein R₃ is as defined in claim 1, and R₅ is a lactone or lactam of the structure

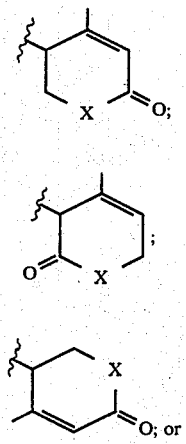

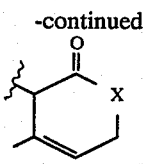

and X is oxygen or NR where R is as defined in claim 1.

7. The retinoid of claim 6 wherein X is oxygen.

8. The retinoid of claim 6 known as 13-cis-12-(hydroxymethyl)retinoic acid δ-lactone and the pharmaceutically acceptable salts thereof.

9. The retinoid of claim 6 known as 13-cis-12-carboxyretinol δ-lactone and the pharmaceutically acceptable salts thereof.

10. The retinoid of claim 6 known as 11-cis,13-cis-12-(hydroxymethyl)retinoic acid δ-lactone and the pharmaceutically acceptable salts thereof.

11. The retinoid of claim 6 known as 11-cis,13-cis-12-carboxyretinol δ-lactone and the pharmaceutically acceptable salts thereof.

* * * * *